United States Patent [19]

Smith et al.

[11] Patent Number: 4,934,363

[45] Date of Patent: Jun. 19, 1990

[54] LENS INSERTION INSTRUMENT

[75] Inventors: Gregory M. Smith, Rowland Heights; Ernest Aguilera, Diamond Bar; Howard Newman, Los Angeles, all of Calif.

[73] Assignee: Iolab Corporation, Claremont, Calif.

[21] Appl. No.: 132,292

[22] Filed: Dec. 15, 1987

[51] Int. Cl.⁵ .............................................. A61F 2/16
[52] U.S. Cl. ........................................ 606/107; 623/6
[58] Field of Search ................... 128/303 R, 321, 354, 128/1 R; 604/57, 59, 60, 104, 106, 107, 164, 170; 623/6

[56] References Cited

U.S. PATENT DOCUMENTS

| | | | |
|---|---|---|---|
| 4,198,980 | 4/1980 | Clark | 128/303 R |
| 4,325,375 | 4/1982 | Nevyas | 128/321 |
| 4,573,998 | 3/1986 | Mazzocco | 623/6 |
| 4,600,003 | 7/1986 | Lopez | 128/303 R |
| 4,607,617 | 8/1986 | Choyce | 128/305 |
| 4,642,090 | 2/1987 | Utrata | 128/305 |
| 4,674,500 | 6/1987 | De Satnick | 128/305 |
| 4,681,102 | 7/1987 | Bartell | 623/6 |
| 4,711,638 | 12/1987 | Lindstrom | 128/303 R |
| 4,715,373 | 12/1987 | Mazzocco et al. | 128/321 |
| 4,750,498 | 6/1988 | Graham | 128/303 R |
| 4,759,359 | 7/1988 | Willis et al. | 128/303 R |
| 4,763,650 | 8/1988 | Hauser | 128/303 R |
| 4,765,329 | 8/1988 | Cumming et al. | 128/303 R |
| 4,781,719 | 11/1988 | Kelman | 128/303 R |
| 4,787,904 | 11/1988 | Severin et al. | 128/303 R |

*Primary Examiner*—Stephen C. Pellegrino
*Assistant Examiner*—Ralph Lewis
*Attorney, Agent, or Firm*—Donal B. Tobin

[57] ABSTRACT

An insertion tool for an intraocular lens including a disposable insertion assembly and a reusable handle. The insertion assembly includes a rigid tube with a collar about its proximal end and a lens holder which slides within the rigid tube and also includes a collar on its proximal end and a paddle on its distal end. The handle includes a hollow barrel connected to the rigid tube collar and a driver barrel inside the barrel connected to the collar of the lens holder. An actuator button slides along the outside of the barrel and extends through a slot in the side of the barrel to engage the drive barrel. A pusher rod may be placed inside the bore of the drive barrel to help hold the lens in position.

21 Claims, 5 Drawing Sheets

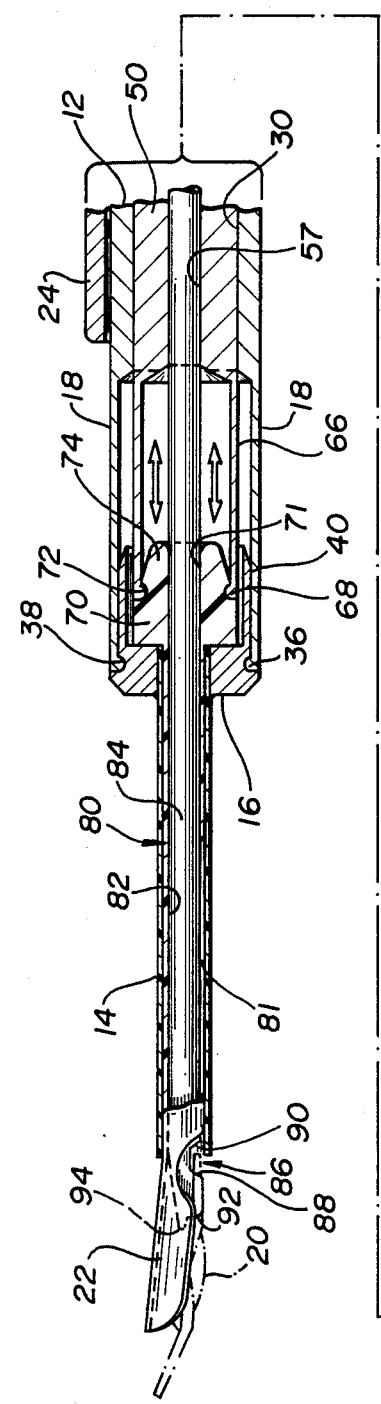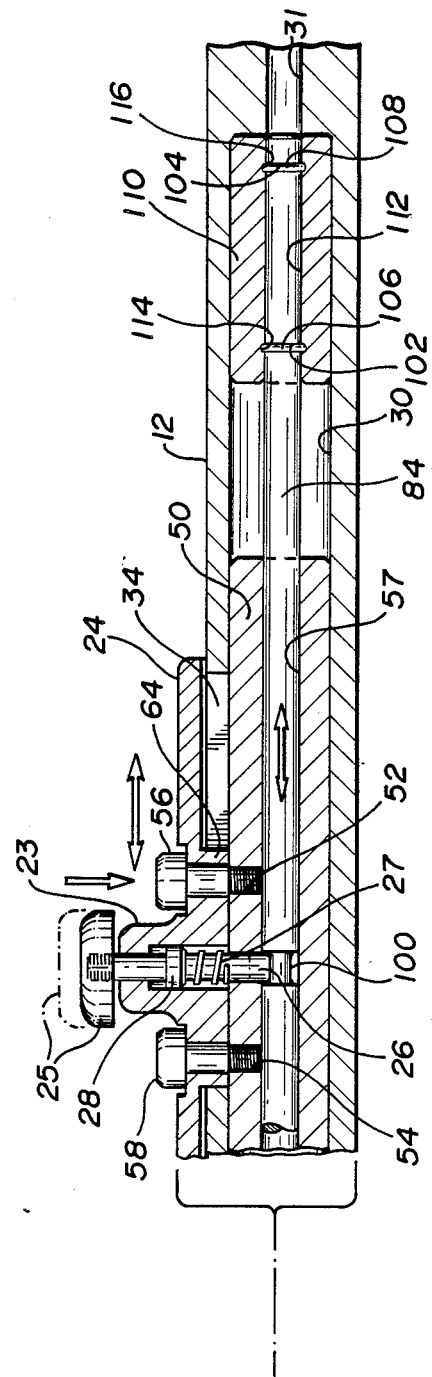
FIG-3

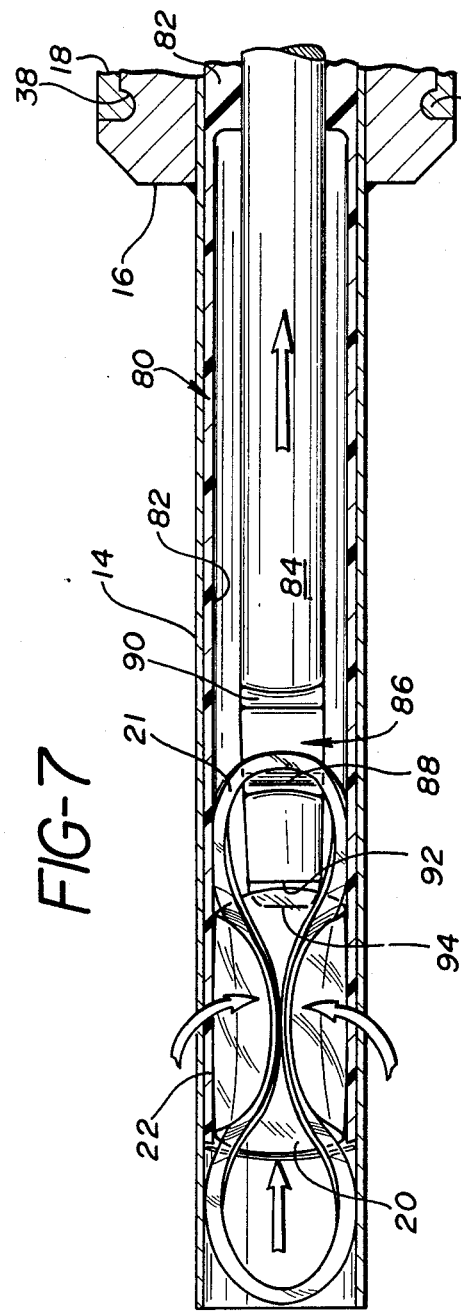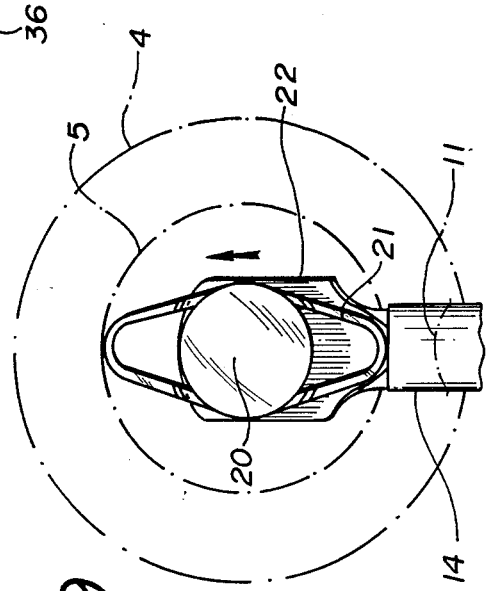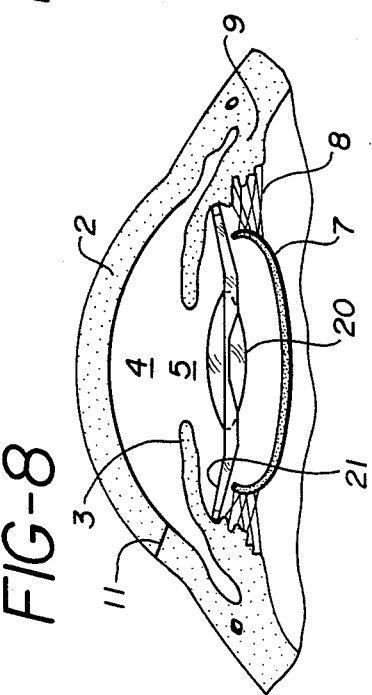

LENS INSERTION INSTRUMENT

FIELD OF THE INVENTION

The present invention relates to a surgical instrument for inserting an intraocular lens into the eye and, more particularly, for inserting a soft foldable intraocular lens through a small incision.

BACKGROUND OF THE INVENTION

When one develops the condition of cataracts, the usually clear natural lens of the eye becomes partially or completely opaque so that the passage of light to the retina is partially or totally inhibited. The problems of cataracts can be substantially alleviated by removing the cataract lens and replacing it with a man made implant.

There is a large variety of possible intraocular lens implants available for use in cataract surgery. There is also a variety of methods for inserting the lens into the eye. Many medical practitioners have expressed a desire to have a tool which would hold the lens during insertion and permit the lens to be inserted through a small incision. A small incision is an incision smaller than the minimum dimension of the outer envelope of the lens when it is in a completely relaxed condition.

Certain intraocular lenses are made of flexible materials like silicone or hydrogel. Such lenses may be folded into a very small shape and inserted through a very small incision. Once the lens is inside the eye it is possible to have the lens relax and expand to its original shape. Certain medical practitioners believe that the smaller the incision through which the intraocular lens implant is introduced into the eye the better. Smaller incisions is believed to create less trauma for the patient and allow the healing process to proceed more quickly. Many procedures which use relatively large incisions, which are larger than the minimum dimension of the envelope of the lens, have been used for many years with satisfactory results. Some believe the smaller incision to provide further and additional benefits, but this is not to suggest that the use of a larger incision is in any way unsatisfactory.

In order to insert a lens through a small incision, it is necessary to reduce the size of the envelope of the lens. It would be convenient to have a tool which can readily reduce the size of the lens for insertion through small incision and then easily release the lens once it is inside the eye.

It would also be desirable to have a reusable portion on the lens insertion tool which could be sterilized and used on a variety of patients and a disposable portion which would come in contact with the lens and with the eye of the patient.

SUMMARY OF THE INVENTION

The present invention provides a surgical instrument for facilitating the insertion of an intraocular lens into the eye. The instrument includes a disposable assembly and a reusable handle with parts for actuating the disposable assembly. The disposable assembly includes an axially extending generally annular rigid tube with a generally annular axially lens holder placed within the rigid tube and capable of reciprocating in the rigid tube. The lens holder includes a paddle portion on its distal end which extends transverse to the axis of the lens holder a distance greater than the largest transverse dimension of the rigid tube. The paddle is preferably made of a flexible film and is adapted to fold to a generally closed position as it is retracted into the rigid tube to hold and at least partially surround the intraocular lens. In the preferred embodiment both the rigid tube and the lens holder include first and second collars affixed to the respective proximal ends of the rigid tube and the lens holder. Each collar has a general annular base portion and includes a generally annular skirt substantially coaxial with its respective rigid tube and lens holder and extends proximally from the collar. The rigid tube and the lens holder are all made of inexpensive preferably plastic materials so that these parts of the instrument may be disposable.

The paddle portion of the lens holder has a slot extending proximally from the paddle portion to a thicker annular sleeve portion which connects to the lens holder collar.

The handle portion of the instrument includes a hollow barrel with a plurality of fingers extending from its distal end designed to removably engage the collar of the rigid tube. There is a slot extending through the side wall of the barrel and an actuator which slides in the slot and a mechanism which projects into the hollow chamber with the barrel. A generally annular drive barrel slides inside the barrel and is connected with the actuator. The distal portion of the drive barrel includes a number of fingers extending from the distal end and designed to be removably connected to the collar portion of the lens holder so that as one moves the actuator along the slot of the barrel, the drive barrel will reciprocate within the barrel and by reason of its connection to the lens holder collar and the rigid connection of the rigid tube to the barrel cause the lens holder to reciprocate within the rigid tube.

A pusher rod may be mounted inside the bore of the drive barrel and extend through the lens holder. A detent block mounted inside the barrel has a bore with a detent recesses which cooperate with detent clips on the proximal end of the pusher rod to help control the motion of the pusher rod with respect to the drive barrel. The distal end of the pusher rod includes a notch to help hold a lens in position during insertion into the eye.

BRIEF DESCRIPTION OF THE DRAWINGS

These and other features of the present invention will become apparent from the following description of certain embodiments of the invention taken in conjunction with the following drawings.

FIG. 3 shows a cross-sectional view of the instrument of FIG. 1;

FIG. 7 shows a cross-sectional view of the distal end of the instrument of the present invention, partly in section, with the lens in position and ready for insertion into the eye;

FIG. 8 shows a sectional schematic view of the anatomy of the eye; and

FIG. 9 shows a schematic plan view of the anatomy of the eye with the instrument being used to insert an intraocular lens as viewed from the back of the eye looking forward.

DETAILED DESCRIPTION OF THE PREFERRED EMBODIMENT

Figure 1:
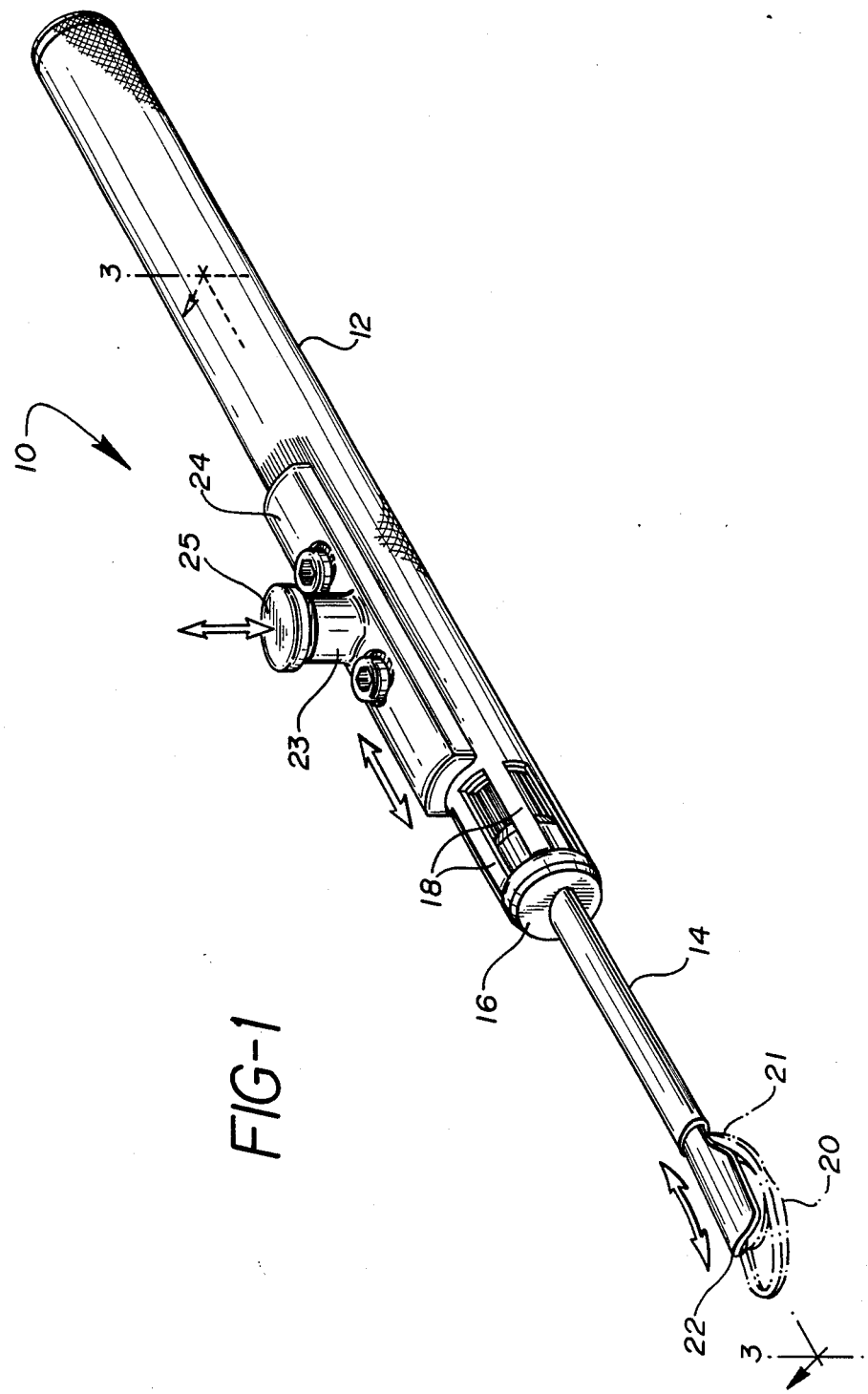
FIG. 1 shows a perspective view of the instrument.

Referring now to FIG. 1 therein shown the surgical instrument 10 of the present invention including a barrel 12 which is preferably a reusable piece made of stainless steel or some other durable and sterilizable material. A rigid tube 14 preferably made of a disposable plastic extends distally from a generally annular collar 16 which is releasably secured to the distal end of barrel 12 by means of flexible fingers 18 as will be more fully described later in the application.

A lens 20 is shown in phantom in paddle portion 22 for the lens holder 80 which extends into rigid tube 14 and can be retracted to bring lens 20 completely within tube 14 for insertion into the eye as will be explained later in the application.

An actuator or slider 24 slides axially along the outside surface of barrel 12 to operate a mechanism within barrel 12 as will be described later in the application. Slide 24 includes a hollow turret 23 to hold spring loaded push button 25. Push button 25 is threaded onto shaft 26 which projects through slot 34 into chamber 30 and is biased out of chamber 30 by spring 27 as it pushes flange 28 of shaft 26 against the inside of hollow turret 23.

Figure 2:
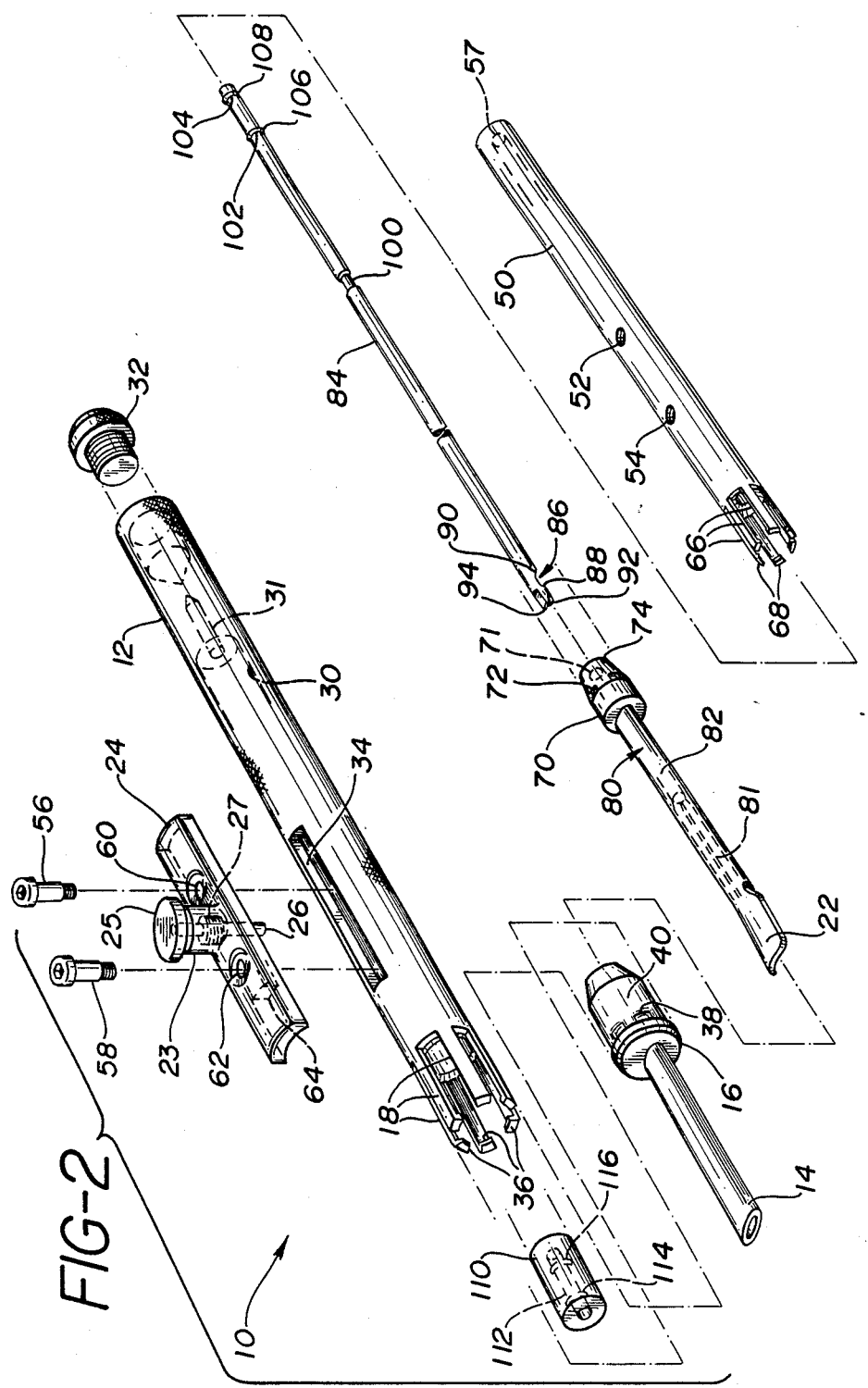
FIG. 2 shows an exploded perspective of the instrument of FIG. 1.

Referring now to FIG. 2 there is shown an exploded perspective view of one embodiment of the present invention. Barrel 12 is a hollow tube with a cylindrical chamber 30 with a proximal tube portion 31 communicating with chamber 30. The proximal end of barrel 12 is closed by a knob 32 which screws into or is press fit into barrel 12 to provide a finished appearance to barrel 12. Slot 34 extends axially along and through the wall of barrel 12 to allow the mechanisms associated with slider 24 access to other elements housed within barrel 12. Fingers 18 extend distally from the distal end of barrel 12 and include at their end inward projections 36. Projections 36 mate with corresponding depressions 38 around the periphery of collar 16 to removably hold disposable collar 16 and rigid tube 14 in place in the distal end of barrel 12. The projections 36 on fingers 18 could be replaced by recesses and correspondingly the recesses 38 on collar 16 could be replaced by projections.

Collar 16 has a skirt 40 extending proximally from collar 16 to help keep collar 16 properly aligned within fingers 18 of barrel 12.

Drive barrel 50 is a generally annular preferably reusable piece which slides with a clearance fit within chamber 30 of barrel 12. Threaded bores 52 and 54 in the side wall of drive barrel 50 receive bolts 56 and 58, respectively. Bolts 56 and 58 are shoulder bolts where only a portion of the shaft is threaded and the other portion is smooth so as to provide a bearing surface as it projects through openings 60 and 62 respectively, in slider 24 through slot 34 into engagement with threaded bores 52 and 54 to connect slider 24 together with drive barrel 50. Thus, as slider 24 moves axially along the outside surface of barrel 12, drive barrel 50 will move with it a distance controlled by the length of slot 34. Drive barrel 50 is hollow with an axial bore 57 extending throughout its length.

Referring now to FIG. 3 is can be seen that the inside of slider 24 includes a boss 64 with a transverse dimension that provides a sliding fit in slots 34 and a longitudinal dimension that controls the distance which slide 24 may move in slot 34.

Referring again to FIGS. 2 and 3, the distal end of drive barrel 50 includes fingers 66. The distal end of each finger 66 includes an inward projection 68.

Attached to the proximal end of lens holder 80 is a generally annular collar 70 which includes depressions 72 which mate with projection 68 on the ends of finger 66 so that collar 70 may be removably attached to drive barrel 50. Collar 70 also includes a skirt 74 much like the skirt 40 on collar 16 so that collar 70 will be properly aligned when it is inserted within finger 66 of drive barrel 50. Extending distally from collar 70 is a lens holder 80.

Lens holder 80 comprises a preferably hollow, rigid, plastic sleeve 82 as can be seen best in FIG. 7. Paddle 22 extends from sleeve 82 of lens holder 80 and is preferably a thin transparent film bonded about the periphery of sleeve 82. The use of a transparent film for paddle 22 permits the user to easily inspect the lens while it is being held in the paddle 22. In the preferred embodiment, collar 70, lens holder 80 including sleeve 82 and paddle 22 are all formed integrally as one part.

Figure 5:
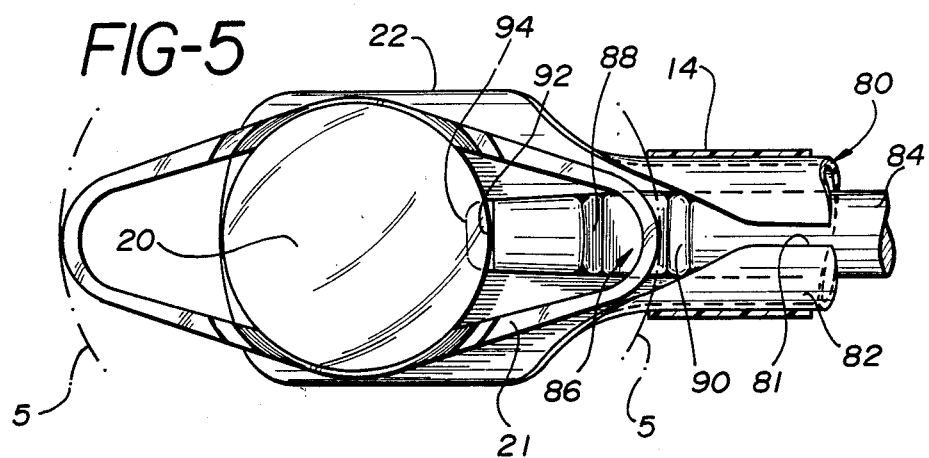
FIG. 5 shows a top plan view of the distal end of the instrument of FIG. 1, partly in section, with an intraocular lens in position.
Figure 6:
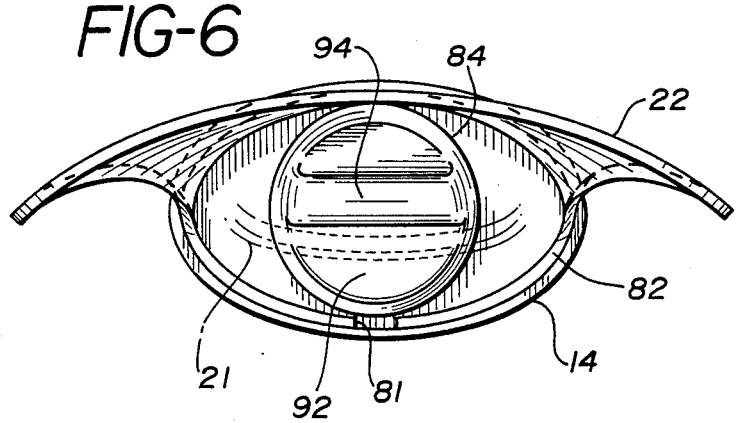
FIG. 6 shows a front view of the distal end of the instrument of FIG. 1 without the lens for purposes of clarity.

Lens holder 80 includes a slot 81 shown best in FIGS. 5 and 6 to facilitate the easy folding of paddle 22 about lens 20 as lens holder 80 is retracted into rigid tube 14. Slot 81 extends axially along lens holder 80 for substantial portion of its length until paddle 22 meets sleeve 82.

Collar 70, rigid tube 14 and collar 16 may be made of any suitable metal or plastic material.

Figure 4:
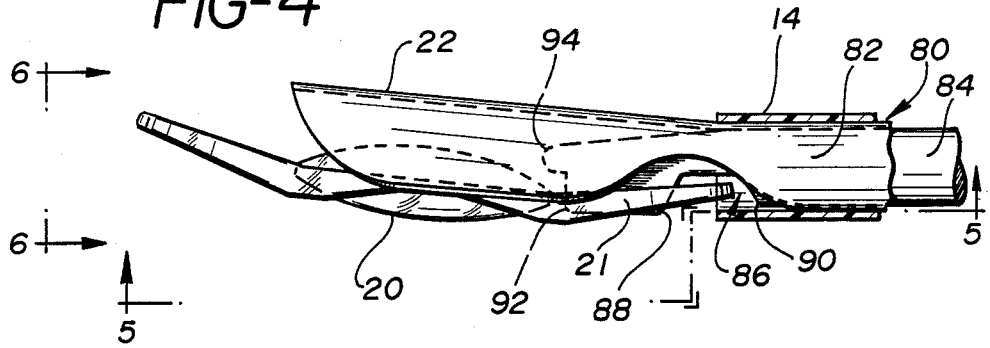
FIG. 4 shows a side elevation, partly in section, of the distal end of the instrument of FIG. 1 with an intraocular lens in position as it is ejected into the eye.

Referring again to FIGS. 3 and 7, there is shown a pusher rod 84 mounted with a sliding fit within bore 57 of drive barrel 50 and extending further through bore 71 in collar 70, through sleeve 82 of lens holder 80 and into paddle 22. Pusher rod 84 has a notch 86 near its proximal end to receive a portion of intraocular lens 20 as best shown in FIG. 4. Notch 86 extends transversely completely across the distal end of pusher rod 84. The distal and proximal ends 88 and 90, respectively, of notch 86 are beveled to facilitate the exit of lens 20 from notch 86, as will be explained later in the application. The free end 92 of pusher rod 84 is aligned generally perpendicular to the axis of pusher rod 84 and includes a rounded projection 94. The dimensions of notch 86 are made to accommodate the specific intraocular lens 20 which this instrument 10 is designed to insert and may be varied to accommodate different intraocular lenses.

Pusher rod 84 includes a generally annular recess at 100 to receive shaft 26 when push-button 25 on slider 24 is depressed by the user. It can be seen from FIG. 3 that when push-button 25 is depressed and shaft 26 is inserted in recess 100 of pusher rod 84 and drive barrel 50 will move together with slider 24 as slider 24 is moved back and forth in slot 34 of barrel 12.

The proximal end of pusher 84 includes two additional recesses 102 and 104 for receiving spring detent clips 106 and 108.

As shown in FIGS. 2 and 3, detent block 110 is pressed fit into the proximal end of chamber 30 and includes a hollow bore 112 and two spaced apart annular detent recesses 114 and 116 for selectively receiving detent springs 106 and/or 108 during the operation of instrument 10 which will be explained later in the application.

Instrument 10 is used to insert an intraocular lens into the eye. A schematic illustration of a cross section through the eye is shown in FIG. 8. Cornea 2 is the front surface of the eye. Iris 3 divides the front portion of the eye into the anterior chamber 4 and the posterior chamber 6. Iris 3 is a sphincter which opens and closes in response to light and defines the pupil 5 through which light is transmitted to the posterior chamber. The capsular bag 7 encapsulates the natural lens of the eye and is preferably left in palce after cataract extraction. Capsular bag 7 is supported by suspensory ligaments or zonuals 8 from ciliary muscle 9. Lens 20 is preferably placed either within capsular bag 7 or is supported by ciliary muscle 9 behind iris 3. An incision 11 is shown in FIG. 8 through which lens 20 may be inserted into the eye using instrument 10 of the present invention.

The operation of instrument 10 and the procedure for inserting lens 20 into the eye using instrument 10 will now be described. Referring now to FIGS. 4–6 and particularly FIG. 5, the user removes the intraocular lens 20 from its package, picks it up with forceps (not shown) and places lens 20 in paddle 22 with one haptic support portion 21 placed in notch 86 of pusher rod 84. Lens 20 craddled in paddle 22 so the user may inspect the lens prior to insertion. While holding the lens with the forceps (not shown), the user may partially feed the lens into rigid lens 14 while retracting pusher rod 84 and drive barrel 50 together into rigid tube 14. To accomplish this retraction, the user pushes down on a push-button 25 so as to engage shaft 26 in recess 100 of pusher rod 84 and retract slider 24 proximally in the direction toward end knob 32 on barrel 12. Pusher rod 84 will retract through detent block 110 and detent spring 106 and 108 will move distally into proximal portion 31 of chamber 30 in barrel 12. Spring detent 106 will move from detent recess 114 proximally into detent recess 116 and spring detent 108 will slide into proximal portion 31 of chamber 30. The forces which spring detent clips 106 and 108 exert on detent recesses 114 and 116 in detent block 110 are small so that pusher rod 84 can be conveniently moved proximally when desired but is strong enough to keep pusher rod 84 from moving independently when push-button 25 is released and spring 27 biases shaft 26 out of recess 100 in pusher rod 84.

As lens holder 80 retracts into rigid tube 14, paddle 22 will fold around the periphery of lens 20. The combined action of the feeding by the user with forceps (not shown) and the action of notch 86 on haptic 21 of lens 20 will help pull lens 20 within tube 14 as pusher rod 84 is retracted. Paddle 22 provides sufficient friction against the material of which lens 20 is made (preferably silicone or hydrogel) to help hold lens 20 frictionally in place. Thus, lens 20 may be fully retracted within rigid tube 14.

Please note that instrument 10 is shown in FIG. 4 in the position for ejecting lens 20 into the eye. When lens 20 is loaded into paddle 22, instrument 10 is rolled over 180° so that lens 20 sits in and on top of paddle 22 to permit the user to inspect lens 20 and feed it into rigid tube 14.

Lens 20 is now ready for insertion into the eye using instrument 10. With lens 20 inside tube 14, instrument 10 may be rolled over from its position in FIG. 4 to that shown in FIG. 1 so that when lens 20 is ejected, paddle 22 will be positioned between cornea 2 and lens 20 to protect the inside of cornea 2. Rigid tube 14 of instrument 10 is then inserted through incision 11 in cornea 2. As shown in FIG. 9, the distal end of rigid tube 14 is inside the anterior chamber over iris 3. The user may wish to position instrument 10 so that at least part of lens 20 will be placed behind iris 3 into posterior chamber 6, capsular bag 7 or into the ciliary muscle 9 behind iris 3.

The user then depresses push-button 25 inserting shaft 26 into recess 100 of pusher rod 84 against the force of spring 27 and advances slider 24 distally along slot 34 in barrel 12 so as to push drive barrel 50 and pusher rod 84 distally together and to correspondingly move paddle 22 and lens 20 distally out of rigid tube 14 into anterior chamber 4. Spring detent clips 106 and 108 will also advance distally through detent block 110 until spring detent clip 106 rests in detent recess 114 of detent block 110. The forces exerted by spring detent clips 106 and 108 on detent block 110 are sufficient to give the user tactile sense of the motion of pusher rod 84 distally. The user can feel when when pusher rod 84 has advanced far enough such that spring detent clip 106 is now in detent recess 114. The forward advance of slider 24 in slot 34 is also controlled by the length of slot 34. When boss 64 hits the distal end of slot 34 as shown in FIG. 3 the user knows that the paddle 22 and pusher rod 84 have advanced all the way into the eye so that the lens 20 is in proper position.

The user then releases push button 25 so that shaft 26 comes out of slot 100 in pusher rod 84 under the influence of spring 27. The user then retracts slider 24 retracting drive barrel 50 and lens holder 80 back into rigid tube 14 while leaving pusher rod 84 in place to prevent lens 20 from sliding back into rigid tube 14 as lens holder 80 and paddle 22 are retracted. With lens holder 80 and paddle 22 now retracted completely within rigid tube 14 and pusher rod 84 still projecting out of rigid tube 14 the lens is now released into the of the eye. Spring detent clips 106 and 108 are respectively in detent recesses 114 and 116 of detent block 14. Spring detent clips exert sufficient force to prevent pusher rod 84 from being retracted even though shaft 27 is disengaged from recess 100 of pusher rod 84, under the frictional influence of drive barrel 50 as it slides along pusher rod 84 and retracts proximally. Instrument 10 now may be removed from the eye through incision 11. The user may now position lens 20 in its proper place in the eye by manipulating lens 20 into capsular bag 7 by one of a variety of well known procedures which are irrelevant to the present invention and will not be described. It can be seen that instrument 10 provides an effective way of inserting intraocular lens 20 into the eye.

As previously mentioned barrel 12 and its associated drive barrel 50 along with slider 24 and push button 25 and its associated parts and pusher rod 84 are reusable parts which may be sterilized and used in a subsequent operation. These parts of instrument 10 will be a permanent part of the surgeons instruments. Collar 16 and its associated rigid tube 14 together with collar 70, lens holder 80 and paddle 22 may be disposable parts which can be easily removed from the distal ends of barrel 12 and drive barrel 50 by merely grasping rigid tube 14 when it is in place and pulling rigid tube 14 distally so that fingers 18 of barrel 12 disengage from depressions 38 on collar 16 and correspondingly fingers 66 of drive barrel 50 disengage from depressions 72 on collar 70. The disposable components of instrument 10 may be provided as replaceable parts which are used for one patient and then thrown away.

In an alternative embodiment pusher rod 84 and detent block 110 may be eliminated. They principle purpose of pusher rod 84 is to prevent lens 20 from being drawn back inside rigid tube 14 when lens holder 80 and paddle 22 are retracted back inside rigid tube 14 leaving lens 20 inside anterior chamber 4 of the eye. In this embodiment, push button 25 and its associated shaft 26 and spring 27 can still be used but since pusher rod 84 has been eliminated, push button 25 will provide no function to the operation of the instrument. In this embodiment lens 20 is loaded into paddle 22 of instrument 10 in the same way as in the previous embodiment then retracted into rigid tube 14 as previously discussed. Then instrument 10 is inserted through incision 11 into the anterior chamber of the eye. The user moves slider 24 distally until boss 64 engages the distal portion of slot 34 in barrel 12 moving lens holder 80 forward and ejecting paddle 22 and lens 20 from rigid tube 14 into the anterior chamber 4 of the eye. With lens 20 free of paddle 22, paddle 22 may be retracted into rigid tube 14 by moving slider 24 proximally.

While the present invention has been described in connection with certain preferred embodiments, those skilled in the art will appreciate that certain modifications may be made without departing from the scope of the present invention. It is, therefore, not intended that the present be limited except as set forth in the following claims.

We claim:
1. A surgical instrument for inserting an intraocular lens into the eye comprising:
   an axially extending generally annular rigid tube having a distal end and a proximal end;
   a generally annular axially extending lens holder disposed at least partially within said rigid tube and having a distal end adapted for axially reciprocation within said rigid tube;
   said lens holder including a flexible paddle portion extending from its distal end adapted for retraction into or ejection from said rigid tube, said paddle portion extending transverse to the axis of said lens holder a distance greater than the largest transverse dimension of said rigid tube when said paddle portion is ejected from said rigid tube, and said paddle portion adapted to fold to a generally closed position when retracted into said rigid tube to hold and at least partially surround an intraocular lens;
   wherein said generally annular lens holder includes a slot extending axially along and through the wall of said lens holder from its distal end proximally; and
   wherein said paddle portion of said lens holder is made of a thin, plastic, flexible film.
2. The instrument of claim 1 wherein said lens holder includes a generally annular support sleeve connected to a proximal portion of said paddle portion adapted to reciprocate axially within said rigid tube with said paddle portion and to provide structural support for said paddle portion.
3. The instrument of claim 1 wherein said rigid tube has a generally oval cross-section.
4. The instrument of claim 1 further including means for holding said rigid tube fixed with respect to said lens holder.
5. The instrument of claim 4 wherein said means for holding said lens holder with respect to said rigid tube includes a second collar affixed to the proximal end of said lens holder, including a generally annular base portion, and including a generally annular skirt substantially coaxial with said lens holder and extending proximally from said second collar base.
6. The instrument of claim 5 further including:
   a lens holder drive barrel having a distal end disposed for axial reciprocation with respect to said rigid tube; and
   means for removably connecting the distal end of said lens holder drive barrel to said lens holder in substantially coaxial alignment.
7. The instrument of claim 6 wherein said lens holder drive barrel includes a plurality of fingers extending distantly from the distal end of said lens holder drive barrel;
   means cooperatively disposed on said drive barrel fingers and said lens holder for removably connecting said drive barrel to said lens holder.
8. The instrument of claim 1 further including means disposed respectively on said rigid tube and said lens holder for providing rotational alignment therebetween.
9. The instrument of claim 4 wherein said means for holding said rigid tube includes a first collar affixed to the proximal end of said rigid tube and including a generally annular base portion and including a generally annular skirt substantially coaxial with said rigid tube and extending proximally from said first collar base.
10. The instrument of claim 1 further including a generally annular hollow barrel having a distal end; and
   means for removably connecting the distal end of said barrel to said rigid tube in substantially coaxial alignment.
11. The instrument of claim 10 wherein said barrel includes a plurality of fingers extending distally from the distal end of said barrel; and
   means cooperatively disposed on said barrel fingers and said rigid tube for removably connecting said barrel to said rigid tube.
12. The instrument of claim 10 wherein said lens holder drive barrel includes a plurality of fingers extending distally from the distal end of said drive barrel;
   means cooperatively disposed on said drive barrel fingers and said lens holder for removably connecting said drive barrel to said lens holder.
13. The instrument of claim 1 further including a pusher rod means mounted within said rigid tube and adapted for selectable reciprocation with respect to said rigid tube.
14. A surgical instrument for inserting an intraocular lens into the eye comprising:
   a generally annular barrel having a distal end and having an axis and defining an axially extending hollow chamber;
   a slot extending through the wall of said generally annular barrel;
   a generally cylindrical drive barrel having a distal end disposed within the chamber of said generally annular barrel and adapted for reciprocal movement therewithin;
   actuation means disposed along the outside surface of said generally annular barrel and at least partially projecting through said slot;
   means for connecting said actuation means to said drive barrel so that as said actuation means is moved axially along said slot said drive barrel will move axially within said generally annular barrel;

a rigid axially extending tube having a distal end and a proximal end, the proximal end being adapted for removable connection to the distal end of said generally annular barrel is substantially coaxial alignment;

axially extending lens holder means disposed at least partially within said rigid tube adapted for reciprocation within said rigid tube and adapted for removable connection to the distal end of said drive barrel in substantially coaxial alignment; and said lens holder means including a flexible paddle portion extending from its distal end, adapted for retraction into or ejection from said rigid tube said paddle portion extending in a direction transverse to the axis of said lens holder a distance greater than the largest transverse dimension of said rigid tube when said paddle portion is ejected from said rigid tube, and said paddle portion adapted to fold to a generally closed position when retracted into said rigid tube to hold and at least partially surround an intraocular lens.

15. The instrument of claim 14 wherein said drive barrel has bore extending axially throughout its length;

a pusher rod slideably mounted within said drive barrel bore and adapted for selectable reciprocation therewithin; and said pusher rod including a means for selectably engaging said actuator means whereby said actuator means may selectably engage said pusher rod and said drive barrel together.

16. The instrument of claim 15 wherein said pusher rod is a generally cylindrical rod extending axially within said rigid tube; and retention means near the distal end of said pusher rod for engaging a portion of an intraocular lens.

17. The instrument of claim 16 wherein said retention means includes a recess extending transversely across and spaced proximally from the distal end of said pusher rod for holding said lens in the eye as said lens holder is retracted within said rigid tube.

18. The instrument of claim 17 wherein said means for connecting said actuation means to said drive barrel includes a push-button having a shaft extending through said actuation means through said barrel and into said barrel bore;

biasing means for biasing said shaft out of said drive barrel bore;

means for controlling the rest position of said push-button under the influence of said biasing means so that the end of said shaft is clear of said drive barrel bore when said push-button is in the rest position;

whereby when said push-button is depressed against the force of said biasing means the end of said push-button shaft projects into said pusher rod retention means so that said drive barrel and said pusher rod may move together as a unit when said actuation means moves axially along the said barrel.

19. The instrument of claim 15 wherein said means on said pusher rod for selectively engaging said actuator means includes a cylindrical recess about the perimeter of said pusher rod.

20. The instrument of claim 15 further including a detent block fixedly secured within said barrel chamber and including a bore extending axially therethrough aligned with said drive barrel bore;

the interior surface of said detent block bore including at least one detent recess; at least one spring detent clip disposed about a proximal portion of said pusher rod and adapted to selectively engage said detent block, detent recess;

whereby said pusher rod may remain fixed as said drive barrel moves with respect to said pusher rod, said detent block detent recesses and said pusher rod spring detent clip cooperating to overcome any frictional drag by said drive barrel on said pusher rod as said drive barrel moves with respect to said pusher rod.

21. The instrument of claim 14 wherein said actuation means to said driver barrel includes a push-button means including a shaft projecting through said actuation means and said drive barrel; and biased means for biasing said push-button means in the direction away from said drive barrel.

* * * * *